US00PP30877P2

(12) United States Plant Patent
Sharma et al.

(10) Patent No.: US PP30,877 P2
(45) Date of Patent: Sep. 10, 2019

(54) PISTACHIO ROOTSTOCK NAMED 'UCB1-D15'

(50) Latin Name: ***Pistacia atlantica* X *Pistacia integerrima***
Varietal Denomination: UCB1-D15

(71) Applicants: John Scott Duarte, Modesto, CA (US); Jeffrey Thomas Duarte, Modesto, CA (US)

(72) Inventors: Dharam Sharma, Hughson, CA (US); Kendall Ash, Hughson, CA (US); Javier Castillon, Hughson, CA (US)

(73) Assignees: John Scott Duarte, Modesto, CA (US); Jeffrey Thomas Duarte, Modesto, CA (US)

( * ) Notice: Subject to any disclaimer, the term of this patent is extended or adjusted under 35 U.S.C. 154(b) by 0 days.

(21) Appl. No.: 16/350,696

(22) Filed: Dec. 20, 2018

(51) Int. Cl.
*A01H 6/00* (2018.01)
*A01H 5/08* (2018.01)

(52) U.S. Cl.
USPC ..... Plt./152

(58) Field of Classification Search
USPC ..... Plt./152
CPC ..... A01H 5/08
See application file for complete search history.

(56) References Cited

U.S. PATENT DOCUMENTS

| | | | |
|---|---|---|---|
| PP17,708 | P3 | 5/2007 | Kawashima |
| PP17,758 | P2 | 5/2007 | Bradford |
| PP18,262 | P3 | 12/2007 | Parfitt et al. |
| PP26,915 | P3 | 7/2016 | MacIlvaine et al. |
| PP26,916 | P3 | 7/2016 | MacIlvaine et al. |
| PP27,079 | P3 | 8/2016 | Blackwell |
| PP27,318 | P3 | 11/2016 | MacIlvaine et al. |
| PP27,319 | P3 | 11/2016 | MacIlvaine et al. |
| PP27,436 | P3 | 12/2016 | MacIlvaine et al. |
| PP29,121 | P3 | 3/2018 | Ash et al. |
| PP29,122 | P3 | 3/2018 | Sharma et al. |
| PP29,123 | P3 | 3/2018 | Castillon et al. |
| PP29,125 | P3 | 3/2018 | Brazelton et al. |

OTHER PUBLICATIONS

Blake, Sanden et al, Large-Scale Utilization of Saline Groundwater for Irrigation of Pistachios Interplanted with Cotton (University of California 2009).

Ferguson, et al., Pistachio Production Manual, Fourth Edition 2005, Ch. 8, Pistachio Rootstocks (University of California 2005).

*Primary Examiner* — Keith O. Robinson
(74) *Attorney, Agent, or Firm* — Mark D. Miller

(57) ABSTRACT

Disclosed is a new and distinct variety of pistachio rootstock called 'UCB1-D15' characterized in that it has greater rootstock growth, greater scion growth and superior crop yield.

2 Drawing Sheets

Latin name: *Pistacia atlantica* X *Pistacia integerrima.*
Varietal denomination: 'UCB1-D15'.

CROSS-REFERENCES TO RELATED APPLICATIONS

The present variety was developed as part of a breeding program which produced at least one other pistachio rootstock, 'UCB1-D11' which is the subject of application Ser. No. 16/350,697.

BACKGROUND OF THE NEW VARIETY

The present invention comprises a new and distinct cultivar of hybrid pistachio (*Pistacia atlantica* (not patented) x *Pistacia integerrima* (not patented)) used as a rootstock known by the varietal name 'UCB1-D15.' The variety 'UCB1-D15,' is an in vitro, single selection of the segregating controlled cross of (*P. atlantica* x *P. integerrima*) made at Davis, Calif. The purpose of the selection program was to develop rootstocks that when grafted with common varieties produced superior vigor and crop yields. The present variety exhibits greater vigor and productivity than 'UCB1-D1' (not patented) rootstock. The present variety has higher resistance to Verticillium disease than the female parent, *Pistacia atlantica*. The present variety has higher cold tolerance than the male parent, *Pistacia integerrima.*

The following characteristics distinguish clone 'UCB1-D15' from the industry standard, 'UCB1-D1' (not patented) rootstock:

1. Greater rootstock growth.
2. Greater scion growth.
3. Superior crop yield.
4. The present variety differs from the industry standard 'UCB1-D1' (not patented) rootstock in that it has consistently produced an average yield per acre that is more than double that of 'UCB1-D1', even in non-bearing years. The present variety differs from rootstock 'UCB1-D11' in that the present variety has a slightly smaller rootstock circumference, and produces a slightly smaller average yield per acre than the 'UCB1-D11'.

ASEXUAL REPRODUCTION OF THE NEW VARIETY

In 1999, seeds from 'UCB1' were sprouted, tissue cultured, and micro-propagated into plants. Several plants, each from a different seed, were selected based on their ability to be propagated, and grown into small plants in a laboratory. The present variety ('UCB1-D15') is one of the plants that came from one of these seeds that was germinated in culture. That plant of the present variety was then propagated by tissue culture to make many clones. In 2002, approximately five of these clones of the present variety were planted in Kern County, Calif. as rootstock trees onto which 'Kerman' (not patented) scions were grafted. The trees were then grown for several years. In 2014, observations of the five trees were made with encouraging results.

Asexual reproduction of the new and distinct variety of rootstock was accomplished in 2015 by taking shoot tissues from the rootstock part of the trees in the field, introducing the tissues into in vitro culture conditions, and propagating the resulting in vitro shoots using micropropagation techniques. The shoots were sub-cultured and multiplied until desired numbers were obtained and then transferred to rooting stage media. Plantlets were then transferred to a peat:perlite media in acclimation chambers under 100% humidity. Field environmental parameters were gradually introduced to harden plantlets which were then successively transferred to larger pots in the greenhouse as their size increased. These potted trees were planted in 2016 and used to establish field performance trials. Subsequent evaluations have shown those asexual reproductions are true-to-type to the original rootstock selection. All characteristics of the original tree were established and appear to be transmitted completely through succeeding asexual propagations.

SUMMARY OF THE NEW VARIETY

The 'UCB1-D15' rootstock of the present invention is characterized by its greater vigor and productivity. In all test years, in comparison to the industry standard rootstock, 'UCB1-D1' (not patented), the present 'UCB1-D15' variety had greater rootstock growth (approximately 1.23 times as great), greater scion growth (approximately 1.15 times as great), and superior yield (approximately 2.37 times as great).

DESCRIPTION OF THE ILLUSTRATIONS

The accompanying photographic illustrations show typical specimens of vegetative growth of the new variety, with the color being as nearly true as is possible with color illustrations of this type:

DESCRIPTION OF THE NEW VARIETY

Figure 1:
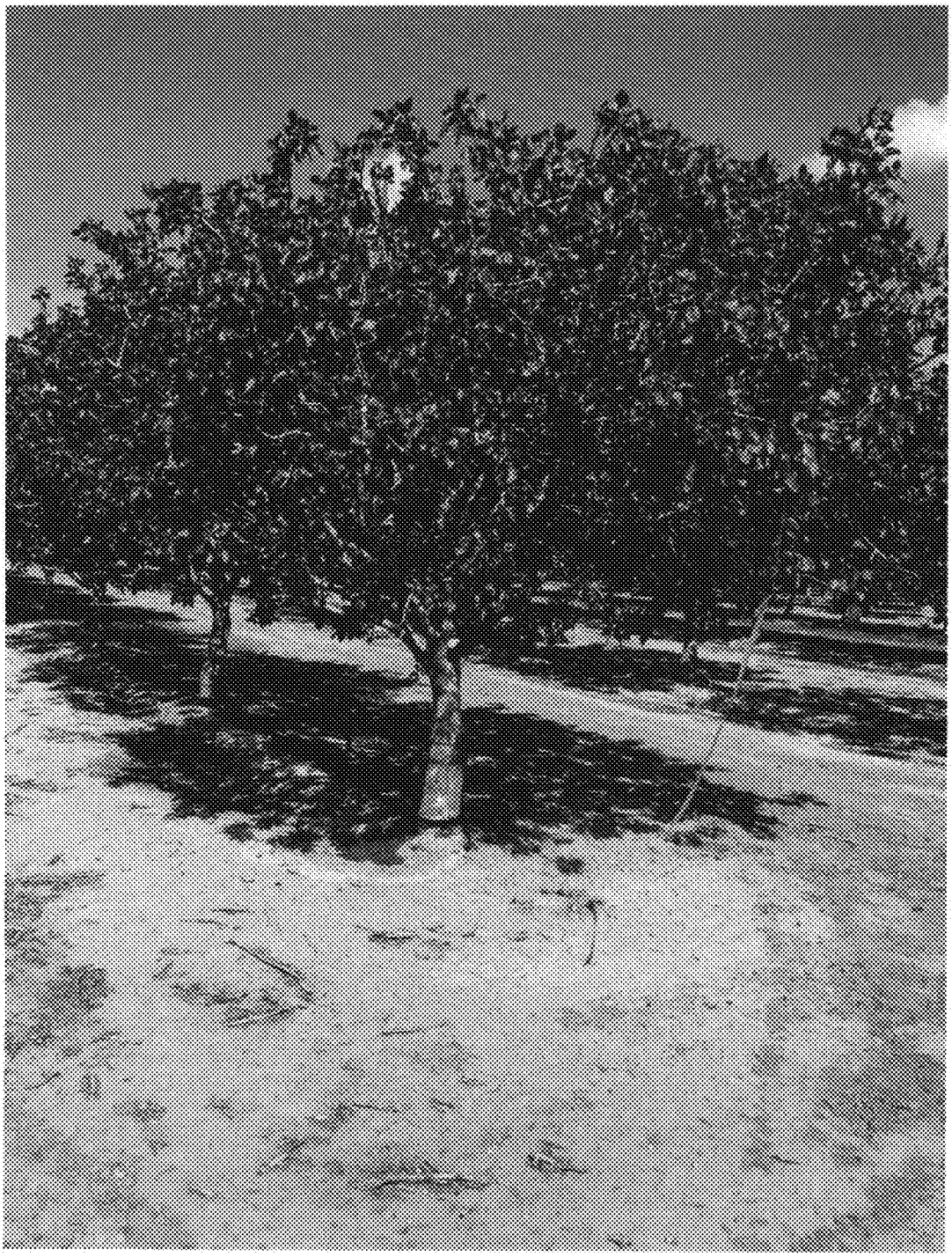
FIG. 1 shows a 16-year old pistachio tree having a rootstock of the new variety.
Figure 2:
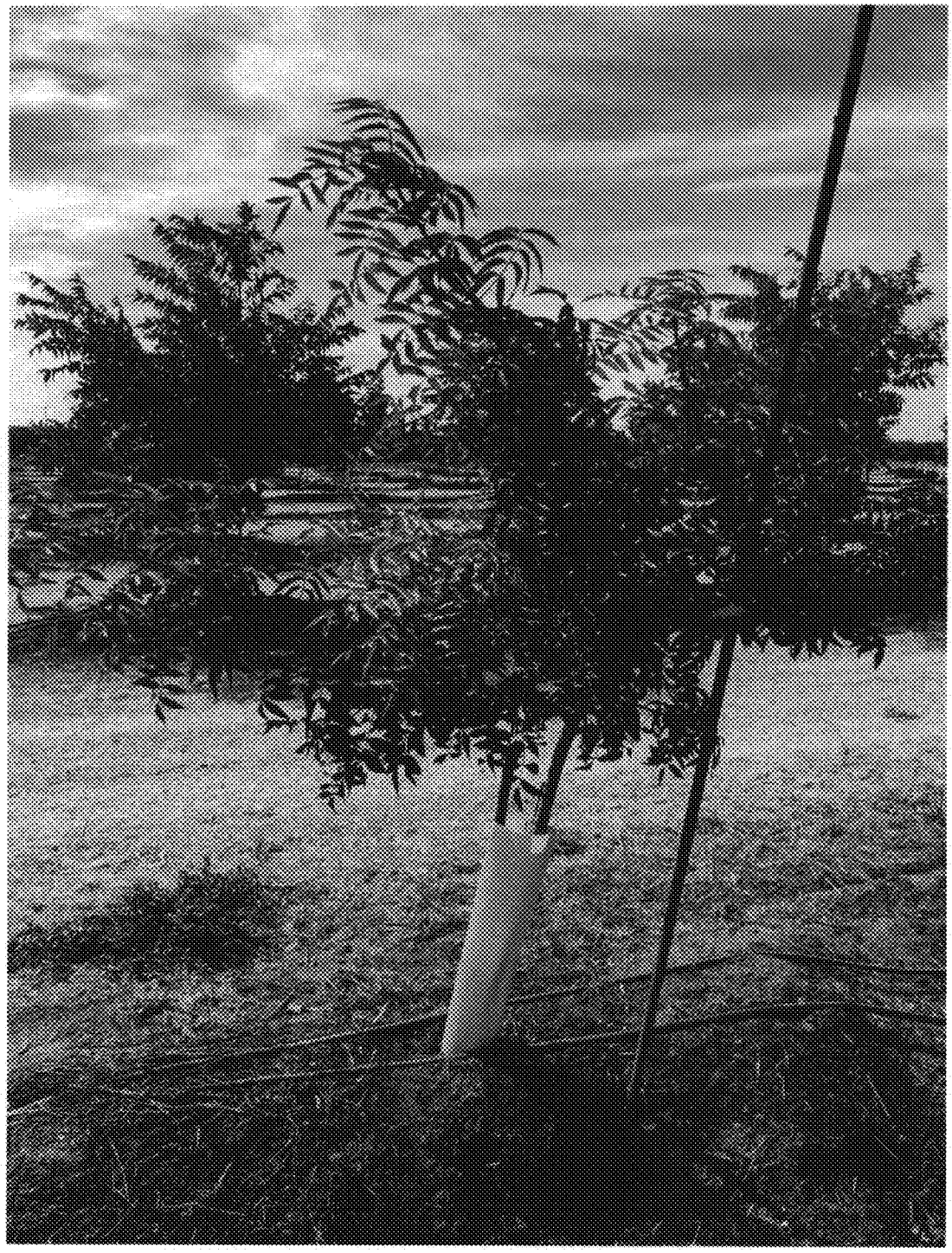
FIG. 2 shows a 2-year old tree of the new variety.

The following detailed description sets forth the characteristics of the new variety. The data which defines these characteristics was collected under natural daylight on plants grown in the field in the central valley of California in Stanislaus County. Descriptions may vary in slight detail due to climatic, soil and cultural conditions under which the variety may be grown. Color designations are presented with reference to the Inter-Society Color Council, National Bureau of Standards published in 1976, except where common color names are also included.

TREE

Tree height at approximately 2 years of age averages 41.8 in.

Trunk bark color is grayish olive [110.g.O].

Trunk diameter at 24 inches above soil surface averages 7.5 mm.

Trunk Lenticels were too small to measure at the time of data recording but are circular in shape and light olive brown [94.1.OB] in color.

On 16-year old tree, trunk bark is smooth.

FOLIAGE

Leaves are pinnately compound composed of alternate leaflets numbering between 10 and 13.

Compound leaf size variations are great but average approximately 25 cm in length and 22 cm in width.

Young leaflets are glossy and very deep red [14.v.d.R] on the upper surfaces and dark red [16.d.R] on the lower surfaces.

Older leaf surfaces are dark olive green [126.d.OG] on upper surfaces and moderate olive green [125.m.OG] on the lower surfaces.

Leaflet shape is lanceolate with an acute apex and cuneate base.

There is significant variation in leaflet size depending on the position on the tree. Leaflet size varies considerably but averages 5.0 cm in length and 1.8 cm in width.

Leaflet venation pattern is pinnate and venation is strong yellowish green [131.s.y.G]. The midrib is prominent and the same color as the venation pattern.

Leaflet margins are entire and surfaces are glabrous.

Petiole and rachis upper and lower surface colors are the same which are predominately strong purplish red [255.s.p.R] with some strong yellowish green [131.s.y.G] streaking on lower surfaces.

Petiole length varies considerably but averages 103 mm in length from point of rachis attachment to basal leaflet and is glabrous with no wings.

Rachis length varies considerably and averages 134 mm in length.

Having thus described and illustrated the new variety of rootstock, what is claimed as new and desired to be secured by plant letters patent is:

1. A new and distinct variety of pistachio rootstock substantially as illustrated and described called 'UCB1-D15' characterized in that, when compared to the industry standard 'UCB1-D1' rootstock, it has greater rootstock growth, greater scion growth and superior crop yield.

* * * * *